US010209333B2

(12) United States Patent
Chung et al.

(10) Patent No.: US 10,209,333 B2
(45) Date of Patent: Feb. 19, 2019

(54) **MAGNETIC RESONANCE IMAGING METHOD USING T2* MAPPING BASED ON ECHO PLANAR IMAGING**

(71) Applicant: GACHON UNIVERSITY OF INDUSTRY-ACADEMIC COOPERATION FOUNDATION, Gyeonggi-do (KR)

(72) Inventors: Jun Young Chung, Incheon (KR); Hyun Wook Park, Daejeon (KR); Ye Ji Han, Daejeon (KR)

(73) Assignee: Gachon University of Industry-Academic Cooperation Foundation, Gyeonggi-Do (KR)

( * ) Notice: Subject to any disclaimer, the term of this patent is extended or adjusted under 35 U.S.C. 154(b) by 796 days.

(21) Appl. No.: 14/432,209

(22) PCT Filed: Apr. 1, 2014

(86) PCT No.: PCT/KR2014/002764
§ 371 (c)(1),
(2) Date: Mar. 29, 2015

(87) PCT Pub. No.: WO2015/119328
PCT Pub. Date: Aug. 13, 2015

(65) Prior Publication Data
US 2016/0041244 A1 Feb. 11, 2016

(30) Foreign Application Priority Data

Feb. 5, 2014 (KR) .................. 10-2014-0013080

(51) Int. Cl.
*G01R 33/50* (2006.01)
*A61B 5/055* (2006.01)
(Continued)

(52) U.S. Cl.
CPC .............. *G01R 33/50* (2013.01); *A61B 5/055* (2013.01); *A61B 2576/00* (2013.01);
(Continued)

(58) Field of Classification Search
CPC .................... G01R 33/4835; G01R 33/50; G01R 33/5616; G01R 33/5615; G01R 33/448; A61B 2576/00; A61B 5/055
(Continued)

(56) References Cited

U.S. PATENT DOCUMENTS

| 5,914,601 A | 6/1999 | Goldfarb |
| 6,541,970 B1 | 4/2003 | Takizawa et al. |

(Continued)

FOREIGN PATENT DOCUMENTS

| JP | H1033501 | 2/1998 |
| JP | H11113877 | 4/1999 |

(Continued)

OTHER PUBLICATIONS

Japanese Office Action for Japanese Application No. 2015-561286, Completed by the Japanese Patent Office, dated Mar. 22, 2016, 4 Pages.

(Continued)

*Primary Examiner* — Rishi Patel
(74) *Attorney, Agent, or Firm* — Brooks Kushman P.C.

(57) ABSTRACT

A flipped fitting method that performs a flipped curve fitting on a maximum of 256 MRI images obtained at different echo times using an EPI image which obtains a plurality of MRI images at a plurality of different echo times within a TR period after application of an excitation RF pulse. Then, T2* values are fitted based on a sufficient amount of acquired TE images, such that it is possible to provide much more accurate T2* values than these provided by underestimated or overestimated fitting by the existing method which is (Continued)

based on only 12 images and to obtain rapid and accurate data without nerve stimulation or acoustic noise. Further, the flipped fitting method is more suitable and accurate for showing the real T2* values.

13 Claims, 7 Drawing Sheets

(51) Int. Cl.
  *G01R 33/48* (2006.01)
  *G01R 33/483* (2006.01)
  *G01R 33/561* (2006.01)

(52) U.S. Cl.
  CPC ........ *G01R 33/482* (2013.01); *G01R 33/4835* (2013.01); *G01R 33/5616* (2013.01)

(58) Field of Classification Search
  USPC .................................................. 324/300–322
  See application file for complete search history.

(56) References Cited

U.S. PATENT DOCUMENTS

| 6,683,453 | B2 | 1/2004 | Heid |
| 6,700,374 | B1 | 3/2004 | Wu et al. |
| 7,795,869 | B1 | 9/2010 | Bydder |
| 2008/0240533 | A1* | 10/2008 | Piron ................... G01R 33/482 382/131 |
| 2010/0171499 | A1 | 7/2010 | Sharp et al. |
| 2010/0280357 | A1 | 11/2010 | Bi et al. |
| 2011/0026799 | A1 | 2/2011 | Nehrke et al. |
| 2012/0161760 | A1* | 6/2012 | Kuhara .................. A61B 5/055 324/307 |
| 2013/0272591 | A1* | 10/2013 | Xue ....................... G06T 11/003 382/131 |

FOREIGN PATENT DOCUMENTS

| JP | 2001008919 | 1/2001 |
| JP | 2002125952 | 5/2002 |

OTHER PUBLICATIONS

Vasylechko et al. Proc. Intl. Soc. Mag. Reson. Med. 2013, vol. 21, p. 918, "T2 measurement of fetal brain using a motion tolerant method".
International Search Report for PCT/KR2014/002764, completed by the Korean Patent Office dated Nov. 20, 2014, 3 Pages.
ESMRMB 2013 Congress, published Oct. 3, 2013, Toulouse, France, Jun-Young Chung, A T2 Mapping Technique Based on Echo Planar Imaging With Full Echoes, 6 pages.
Extended European Search Report for European Application No. EP 14846737.6, Completed by the European Patent Office, dated Sep. 1, 2017, 12 Pages.
Speck et al. Proceedings of the International Society for Magnetic Resonance in Medicine, 6th Scientific Meeting and Exhibition, Apr. 18, 1998, XP040660319, 1 Page, "Functional Imaging by Single Shot I0 and T2 Parameter Mapping".
Clare et al. Proceedings of the International Society for Magnetic Resonance in Medicine, 6th Scientific Meeting and Exhibition, Apr. 18, 1998, XP040660342, 1 Page, "Single Shot T2 Measurement to Establish Optimum Echo Time for fMRI at 3.0T".
Smith et al. Journal of Physics E. Scientific Instruments, vol. 8, No. 6, Jun. 1, 1975, pp. 515-522, XP055400828, "On the design and use of digital filters in certain experimental situations".

\* cited by examiner

MAGNETIC RESONANCE IMAGING METHOD USING T2* MAPPING BASED ON ECHO PLANAR IMAGING

CROSS-REFERENCE TO RELATED APPLICATION

This application is the U.S. national phase of PCT Application No. PCT/KR2014/002764 filed on Apr. 1, 2014, which claims priority to KR Patent Application No. 10-2014-0013080 filed on Feb. 5, 2014, the disclosures of which are incorporated in their entirety by reference herein.

STATEMENT REGARDING GOVERNMENT RIGHTS

This research was partly supported by a grant of the Korea Health Technology R&D Project through the Korea Health Industry Development Institute (KHIDI), funded by the Ministry of Health & Welfare, Republic of Korea (grant number: HI14C1135) and the National Research Foundation of Korea (NRF) Grant funded by Korea Government (MSIP) (no. NRF-2014M3C7033998).

TECHNICAL FIELD

The present invention relates to an imaging method implemented in a magnetic resonance imaging (MRI) system, and more particularly, to a magnetic resonance imaging method using T2* mapping based on echo planar imaging (EPI).

BACKGROUND ART

There are various diagnostic imaging systems such as X-ray, CT, ultrasonic wave, RI image, MRI, and so on. Since the MRI is not harmful to a human body as compared with other diagnostic imaging systems and provides images of the characteristics of structure material inside a human body, the MRI is a very important measuring apparatus in clinical practice.

The MRI apparatus may acquire data on parameters such as spin density, T1, T2, chemical shift, magnetization transfer, chemical exchange saturation transfer, blood stream and spectroscopy, which are unique information on the body, and may acquire various types of body images based on the parameter information.

EPI, which is a high-speed photographing technique capable of acquiring spatial frequency information required for image construction by one radio frequency (RF) pulse within a TR period, is one of the most rapid pulse sequences which are currently being commercialized, and is appropriate for images which are sensitive to a motion and require a fast temporal resolution, such as perfusion images, diffusion images, functional images, and the like.

However, since the EPI method fills the entire K-space within a TR period, there is geometric distortion in the image and therefore a distorted image may be easily obtained.

Further, the EPI method acquires data for one image within about 100 ms and therefore requires much more advanced hardware than that required for a general apparatus. That is, to sample data within the short period of time, there is a need to sufficiently widen and expand the receiving bandwidth, the maximum amplitude of a gradient magnetic field needs to be large, and a strong gradient magnetic field of 10 m T/m or more is generally required. Further, however the strong gradient magnetic field is applied, when a rise time up to the maximum amplitude is long, an image may not be obtained quickly, and therefore a gradient magnetic field apparatus having a slew rate of about 200 to 250 T/ms is required to increase the gradient magnetic field to the maximum amplitude within a short period of time. Further, the data is generated very rapidly in the EPI method, and therefore a high speed receiving apparatus capable of sampling at a rapid speed is required and a large amount of data needs to be processed within a short period of time, and therefore a sufficient amount of RAM is required.

However, the EPI image is deteriorated more than other pulse sequences in terms of a current resolution or contrast, and therefore is not used in a routine method.

Meanwhile, T2* relaxation refers to the decay of transverse magnetization caused by a combination of spin-spin relaxation magnetic field inhomogeneity.

A multi-echo gradient-echo pulse sequence, which is often used for acquisition of images to perform T2* mapping, needs a long scan time and commercialized sequences have limitations, including the number of echoes (a maximum of 12), memory capacity, and the dependency of the fitting functions.

DISCLOSURE

Technical Problem

The present invention is made by recognizing at least any one of the demands or problems which occur in the related art as described above.

An aspect of the present invention provides a method of acquiring an accurate T2* map using EPI.

Another aspect of the present invention provides an echo planar imaging method with full echoes up to 256.

Technical Solution

The embodiment of the present invention performs flipped curve fitting on a maximum of 256 MRI images obtained at different echo times using a method for acquiring an EPI image, which applies an excitation RF pulse and subsequently obtains a plurality of MRI images at a plurality of different echo times. In the process of obtaining the plurality of MRI images, a continuous readout gradient such as a sinusoidal-shaped readout gradient may be applied and an analog to digital converter for data collection signal may be kept in an on state.

According to one aspect of the present invention, there is provided a method for acquiring an image using a magnetic resonance imaging system, including: applying an excitation RF pulse; obtaining a plurality of MRI images at a plurality of different echo times following application of the RF pulse; and performing a flipped curve fitting on the plurality of MRI images.

According to another aspect of the present invention, there is provided a method for acquiring an image using a magnetic resonance imaging system, comprising: applying an excitation RF pulse; obtaining a plurality of MRI images at a plurality of different echo times following application of the RF pulse, wherein in the process of obtaining the plurality of MRI images, a continuous readout gradient is applied.

According to still another aspect of the present invention, there is provided a method for acquiring an image using a magnetic resonance imaging system, comprising: applying an excitation RF pulse; and applying the excitation RF pulse and then obtaining a plurality of MRI images at a plurality of different echo times, wherein in the process of obtaining the plurality of MRI images, an analog to digital converter for data collection is kept in an on state.

The readout gradient may have a sinusoidal shape or a trapezoidal shape, and a navigator echo may be obtained between the applying of the excitation RF pulse and the obtaining of the plurality of MRI images.

The plurality of MRI images may construct a pseudo k-space in which a series of two-dimensional images are arranged according to the echo index.

Advantageous Effects

According to the method for acquiring an MRI image in accordance with the embodiments of the present invention, the T2* values are fitted based on a sufficient amount of acquired TE images, and therefore it is possible to provide more accurate T2* values than those provided by underestimated or overestimated fitting by the existing method which is based on only 12 images.

Further, the method for acquiring an MRI image in accordance with the embodiment of the present invention may rapidly and accurately acquire data without a nerve stimulation or acoustic noise and the flipped fitting method which is used in the embodiment of the present invention may more appropriately and accurately calculate the T2* value.

BEST MODE

Hereinafter, a method for acquiring an image using a magnetic resonance imaging system according to an embodiment of the present invention will be described in detail with reference to the accompanying drawings. However, repeated descriptions and detailed descriptions related to well-known functions or configurations will be omitted herein in order not to unnecessarily obscure the subject matter of the present invention.

The configuration of an MRI system to which the present invention is applied is well known and therefore is omitted herein.

The method for acquiring an MRI image according to the embodiment of the present invention performs a flipped curve fitting on a plurality of MRI images using a method for acquiring an EPI image which applies an excitation RF pulse and then obtains the plurality of MRI images at a plurality of different echo times.

As a frequency selection readout gradient for obtaining the plurality of MRI images, for example, a continuous readout gradient such as a sinusoidal-shaped readout gradient may be applied and an analog to digital converter for data collection signal while the MRI images are acquired needs to be kept at an on state.

Figure 1:
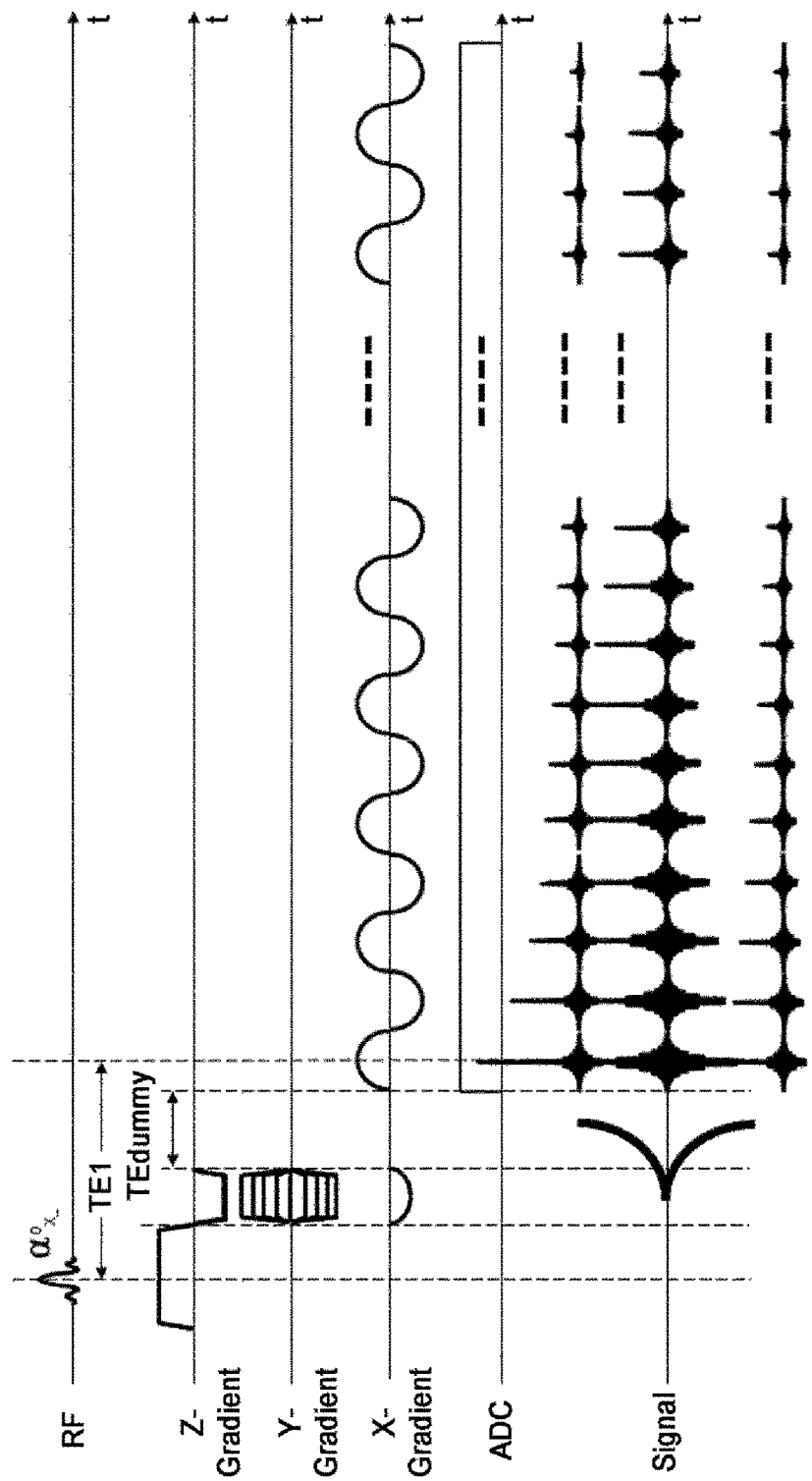
FIG. 1 is a diagram illustrating a pulse sequence which is used in a method for acquiring an MRI image according to an embodiment of the present invention.

FIG. 1 is a diagram illustrating a pulse sequence which is used in a method for acquiring an MRI image according to an embodiment of the present invention.

In FIG. 1, an RF indicates the RF pulse for excitation, a Z-gradient indicates a slice selection gradient, a Y-gradient indicates a phase selection gradient, an X-gradient indicates a frequency selection readout gradient, and an ADC indicates an analog to digital converter for data collection.

As illustrated in FIG. 1, the method for acquiring an MRI image according to the embodiment of the present invention is essentially based on the EPI method which applies the RF pulse once and then obtains several MRI images at the echo times, and the embodiment of the present invention obtains a maximum of 256 full echo images.

As the readout gradient (X-gradient), the sinusoidal-shaped gradient is applied and the ADC is kept in an on state while the full echo images are obtained. In the case of using the sinusoidal-shaped reading gradient, dB/dt, acoustic noise, and eddy current may be reduced.

To evaluate the method for acquiring an MRI image according to the embodiment of the present invention, experiments were performed and the experiment results will be described below.

The experiments were performed on a 3T MRI (Verio) with a 12 channel matrix head coil. In-vivo images were acquired by using the pulse sequence illustrated in FIG. 1. The scan parameters were as follows.

Bandwidth=652 Hz/Pixel
Ramp sampling=ON
TR=550 ms
Total acquisition time=two-and-twenty six minutes
TE=1.8~411.4 ms (256 echoes)
ΔTE=1.6 ms
Slice Thickness=4 mm
FOV=256×256 mm²
Resolution=256×256

Figure 2:
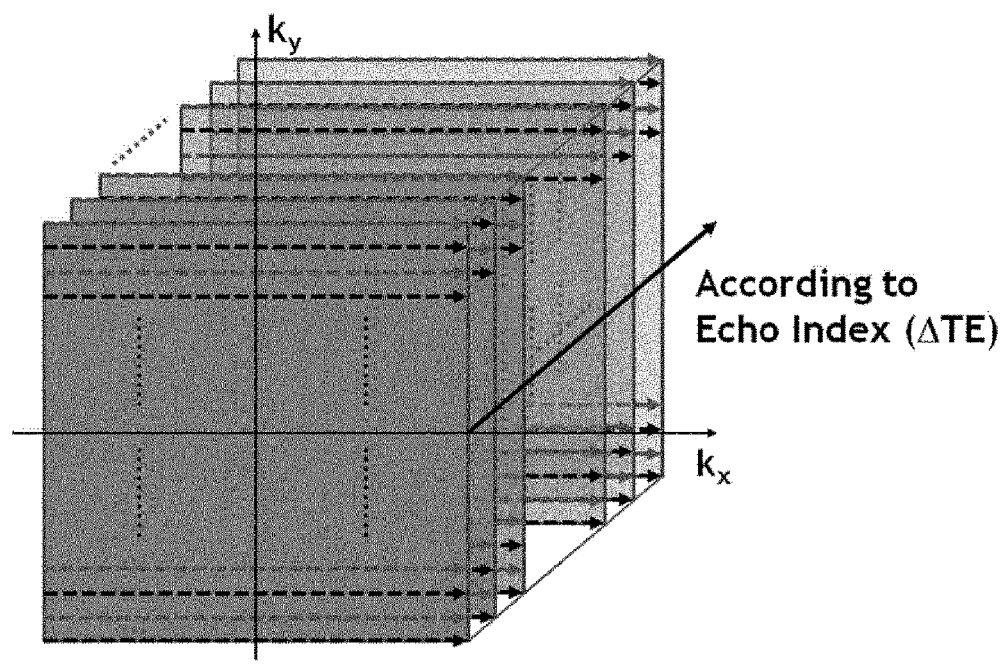
FIG. 2 is a diagram illustrating a pseudo k-space formed by the method for acquiring an MRI image according to the embodiment of the present invention.

Pseudo three-dimensional k-space data as illustrated in FIG. 2 was acquired with the pulse sequence of FIG. 1 and the acquired data was rearranged according to the increment of echo index (TE).

Figure 3:
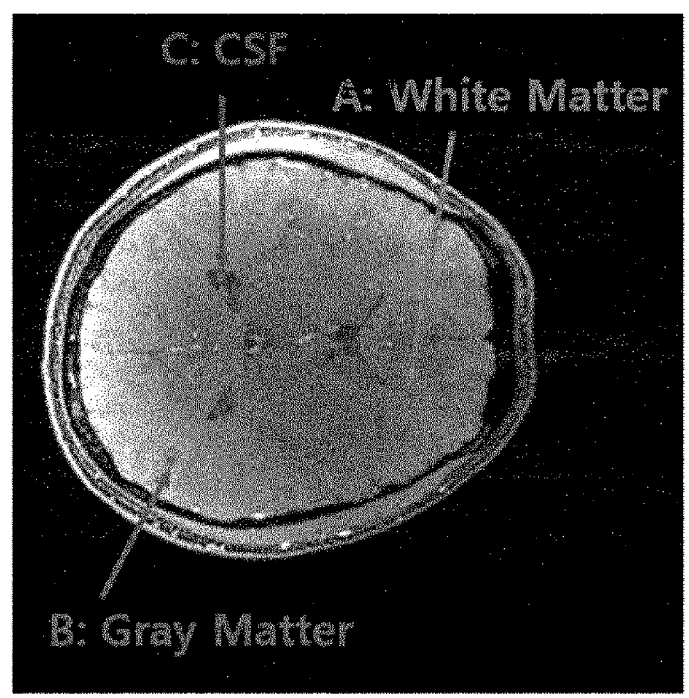
FIG. 3 is a diagram illustrating three regions of interest in a brain.

FIG. 3 is a diagram illustrating three regions of interest of a brain.

As illustrated in FIG. 3, data in three different regions was extracted. A indicates white matter, B indicates gray matter, and C indicates a cerebrospinal fluid (CSF). T2* values were recorded based on the average numerical value within each region of interest (ROI).

Figure 4:
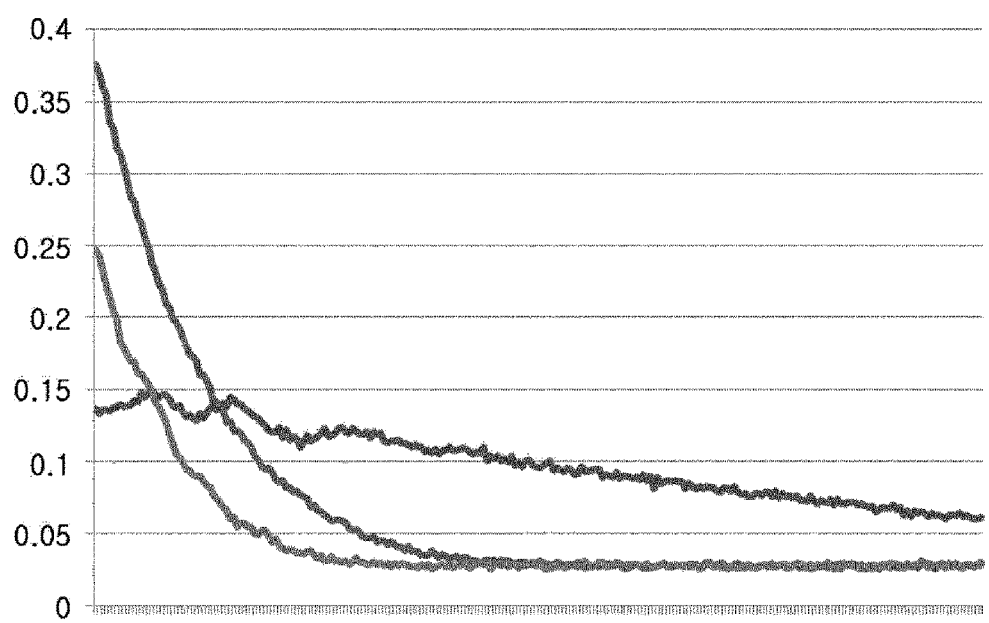
FIG. 4 is a graph of recorded values for each region of interest of FIG. 3.

FIG. 4 is a graph of the recorded values for each region of interest of FIG. 3 and illustrates an actual value in which each region of interest is not subjected to a post-processing process. The data in the CSF region fluctuated abnormally, possibly due to changes in the rate of CSF.

Figure 5:
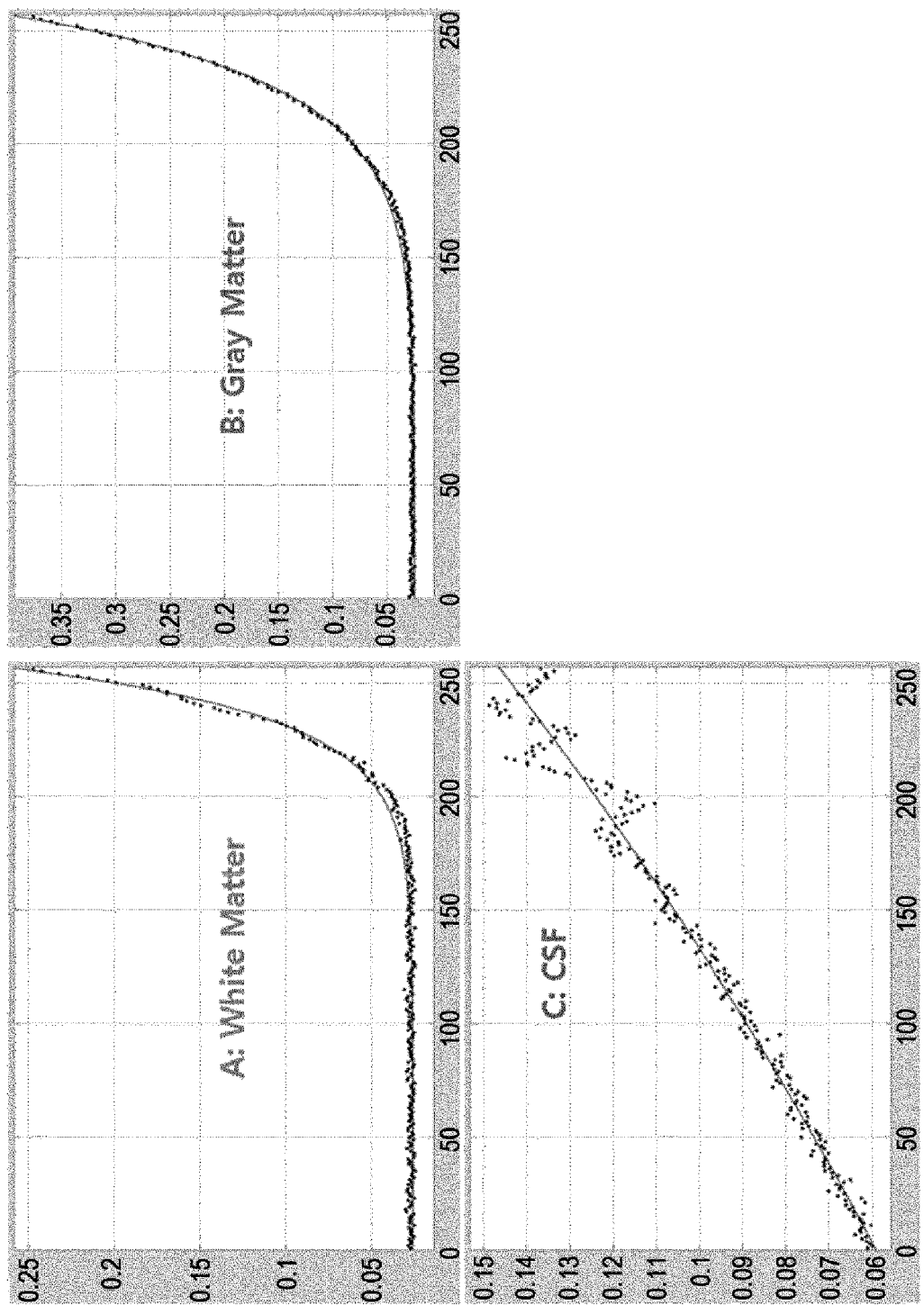
FIG. 5 is a diagram illustrating a fitted curve to original data flipped according to the method of the embodiment of the present invention for each region of interest of FIG. 3.

FIG. 5 is a diagram illustrating fitted curves of the flipped original data according to the method of the embodiment of the present invention, with respect to each ROI of FIG. 3.

An offline reconstruction and curve fitting process were implemented using Matlab (Mathworks). As illustrated in FIG. 5, the reconstructed image indicates a flipped monoexponential fit which is more suitable and accurate for showing the real T2* values.

Errors, such as hardware imperfections, flow, motion, CSF fluctuation, and so on, accumulate from the start point in the fitting process, and initial data is severely distorted and thus it is difficult to perform the fitting. However, when the fitting is performed from the end point of the acquired data by performing a flip as in the method according to the embodiment of the present invention, the curve fitting may be performed accurately even if the distortion is severe.

Meanwhile, the embodiment of the present invention illustrated in FIG. 1 uses a sinusoidal-shaped readout gradient but is not necessarily limited thereto, and therefore for example, a trapezoidal readout gradient may also be used.

Figure 6:
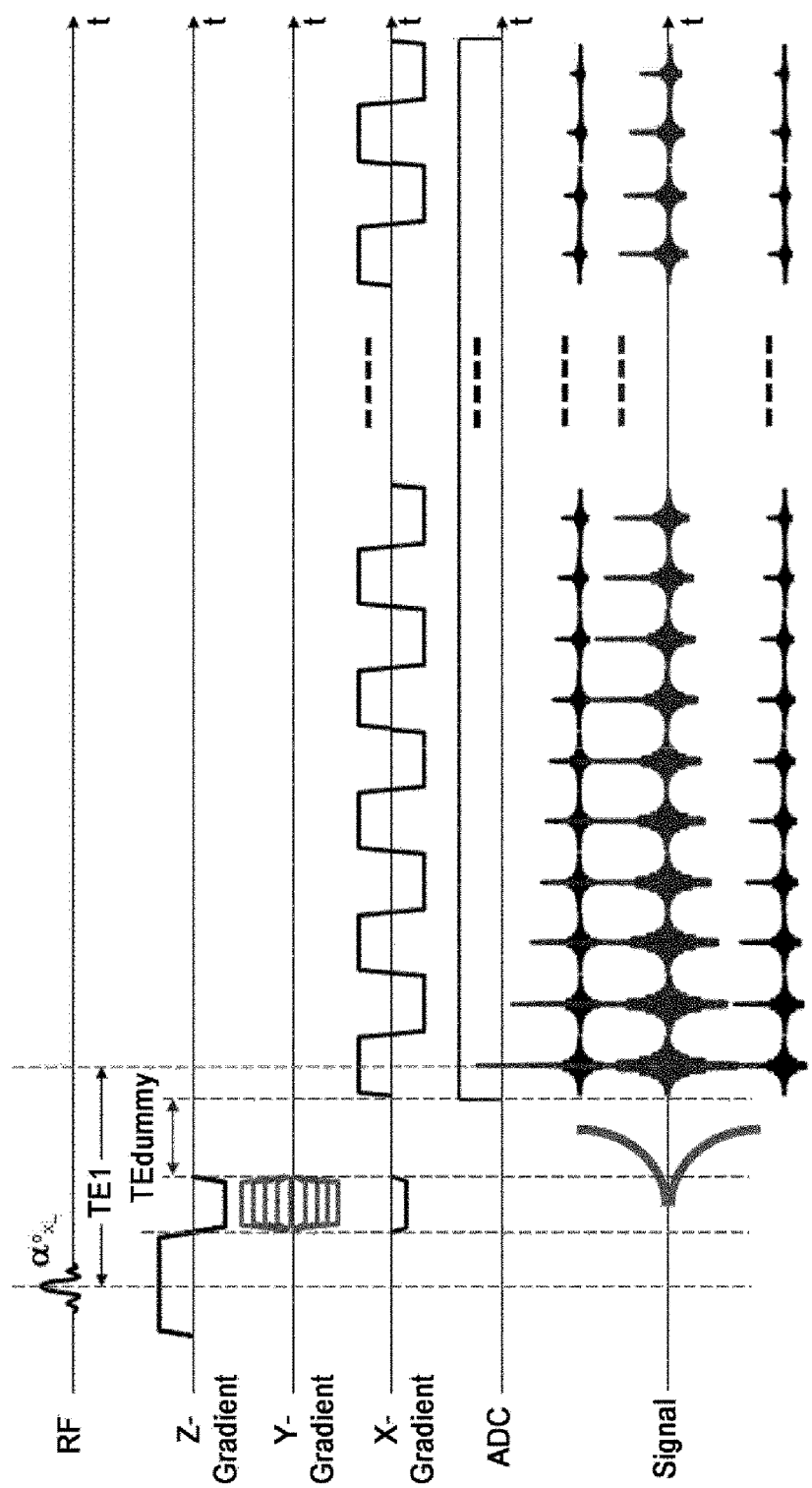
FIGS. 6 to 8 are diagrams illustrating a pulse sequence which is used in a method for acquiring an MRI image according to another embodiment of the present invention.

FIG. 6 illustrates a pulse sequence according to the embodiment of the present invention using the trapezoidal reading gradient. As illustrated in FIG. 6, the remaining portions of the pulse sequence are the same as those illustrated in FIG. 1, but instead of the sinusoidal-shaped reading gradient, a trapezoidal frequency selection readout gradient may be used.

Further, to improve the T2* result value, a navigation echo may also be used.

Figure 7:
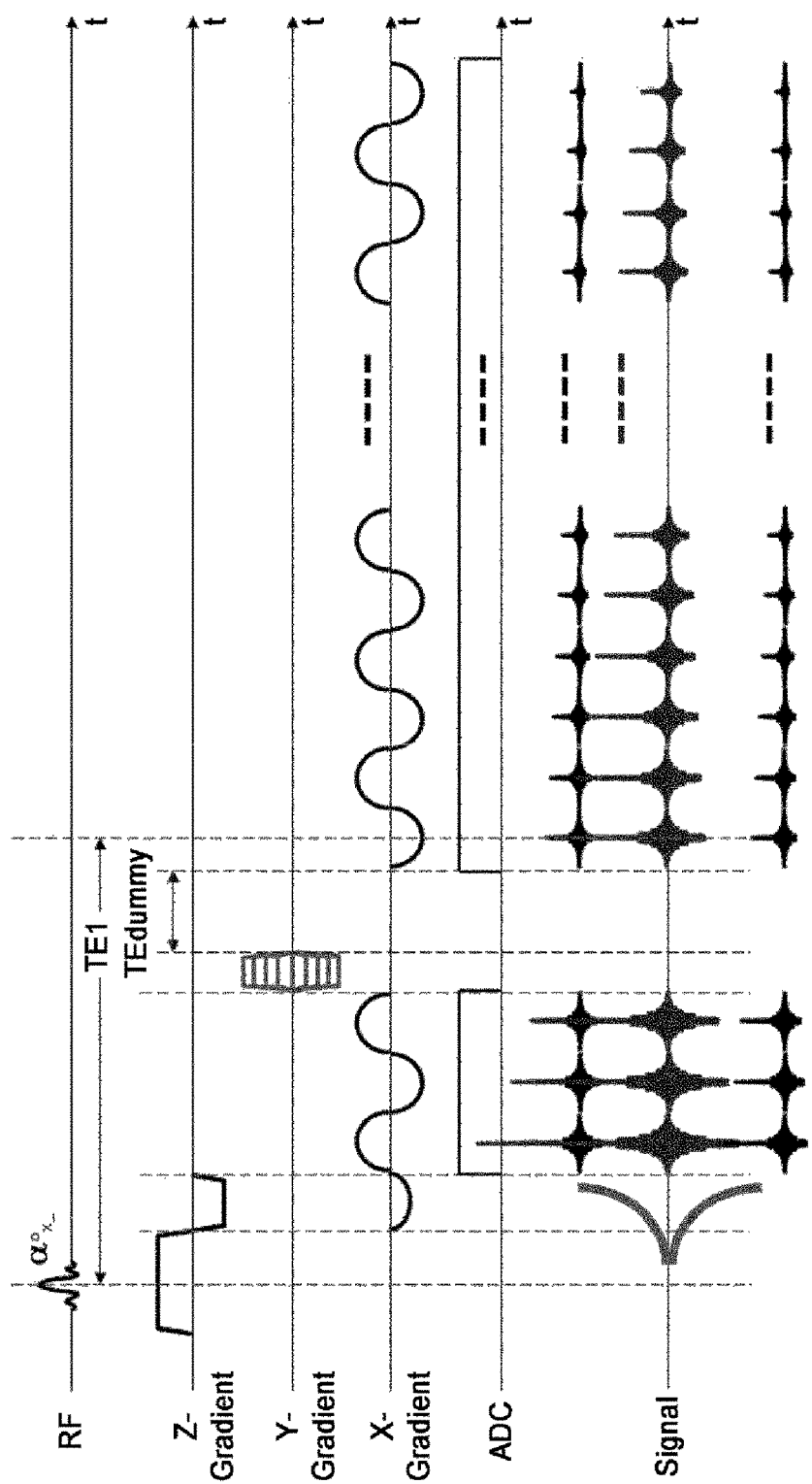
Figure 8:
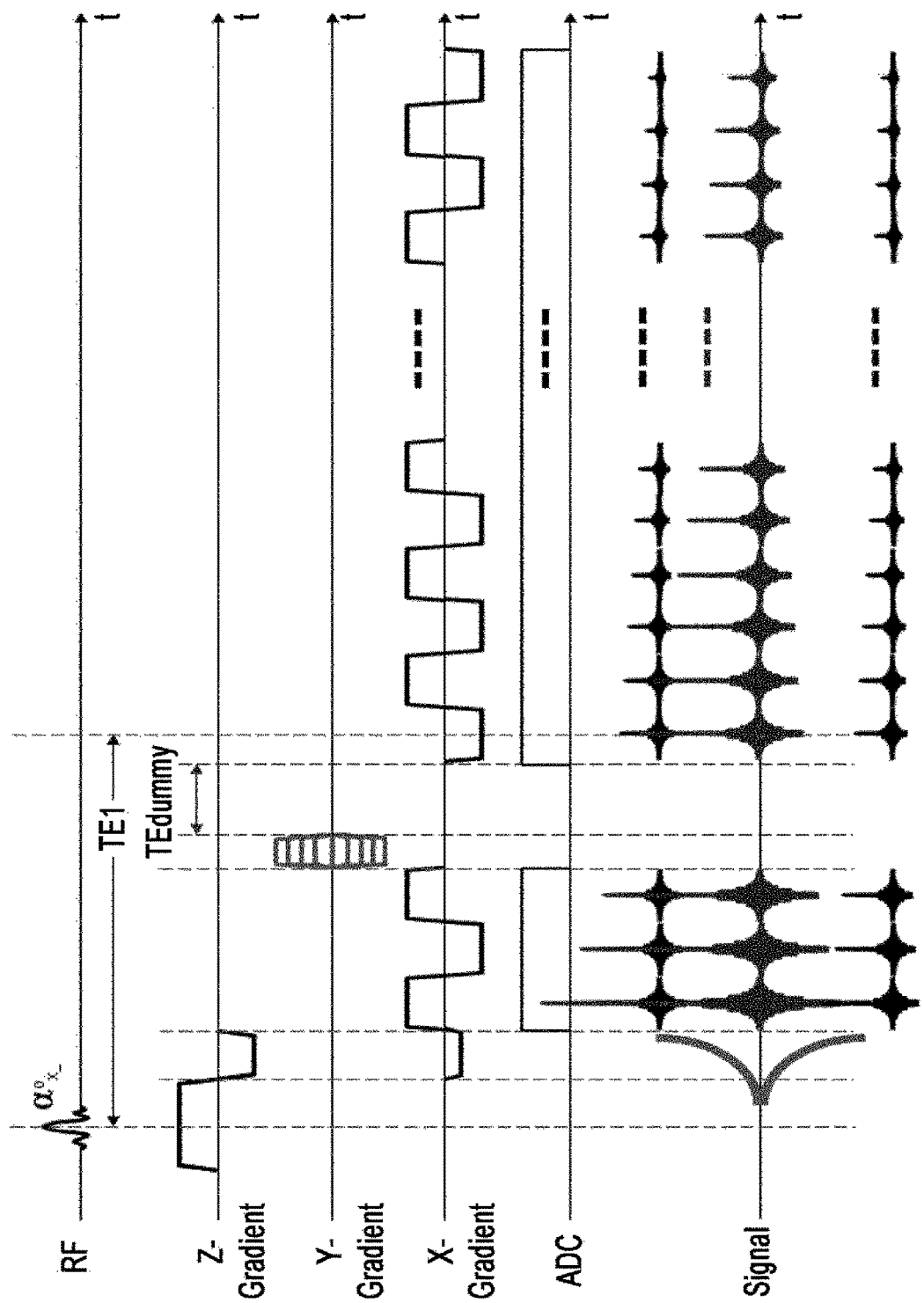

FIGS. 7 and 8 each illustrate the pulse sequence according to the embodiment of the present invention additionally using three navigator echoes in the pulse sequences illustrated in FIGS. 1 and 6.

As described above, the T2* values fitted based on a sufficient amount of acquired TE images as in the embodiment of the present invention provide much more accurate values than values provided by an underestimated or overestimated fitting only based on 12 images according to the existing method.

Further, the method for acquiring an MRI image in accordance with the embodiment of the present invention may rapidly and accurately acquire data without the nerve impulse or acoustic noise and the flipped fitting method may more appropriately and accurately calculate the T2* value.

While the present invention has been shown and described in connection with the exemplary embodiments, it will be apparent to those skilled in the art that modifications and variations can be made without departing from the spirit and scope of the invention as defined by the appended claims.

The invention claimed is:

1. A method for acquiring a plurality of images using a magnetic resonance imaging system, comprising:
    applying an excitation RF pulse;
    obtaining 256 MRI images at a plurality of echo times following application of the excitation RF pulse;
    performing a curve fitting procedure in reverse order to an order of the image obtaining on T2* values derived from the 256 MRI images to generate a T2* map; and
    outputting the T2* map.

2. The method of claim 1, wherein a sinusoidal-shaped readout gradient is applied during the obtaining of the 256 MRI images.

3. The method of claim 1, wherein a trapezoidal-shaped readout gradient is applied during the obtaining of the 256 MRI images.

4. The method of claim 1, wherein an analog to digital converter for data collection signal is kept in an on state during the obtaining of the 256 MRI images.

5. The method of claim 1, further comprising:
    obtaining a navigator echo between the applying of the excitation RF pulse and the obtaining of the 256 images.

6. The method of claim 1, wherein the 256 MRI images define a pseudo k-space in which a series of two-dimensional images are arranged according to an echo index.

7. A method for acquiring a plurality of images using a magnetic resonance imaging system, comprising:
    applying an excitation RF pulse; and
    obtaining 256 MRI images at a plurality of echo times;
    performing a curve fitting procedure in reverse order to an order of image obtaining on T2* values derived from the 256 MRI images to generate a T2* map, wherein a continuous readout gradient is applied during the obtaining of the 256 images; and
    outputting the T2* map for display.

8. The method of claim 7, wherein the continuous readout gradient has a sinusoidal shape.

9. The method of claim 7, further comprising:
    obtaining a navigator echo between the applying of the excitation RF pulse and the obtaining of the 256 images.

10. The method of claim 7, wherein the 256 MRI images define a pseudo k-space in which a series of two-dimensional images are arranged according to an echo index.

11. A method for acquiring a plurality of images using a magnetic resonance imaging system, comprising:
    applying an excitation RF pulse; and
    obtaining 256 images at a plurality of echo times; and
    generating a curve representing T2* values in a region of interest by performing a curve fitting procedure in reverse order to an order of image obtaining on the 256 MRI images,
    wherein an analog to digital converter for data collection signal keeps an on state during the obtaining of the 256 images; and
    outputting the curve for display.

12. The method of claim 11, further comprising:
    obtaining a navigator echo between the applying of the excitation RF pulse and the obtaining of the 256 images.

13. The method of claim 11, wherein the 256 MRI images define a pseudo k-space in which a series of two-dimensional images are arranged according to an echo index.

* * * * *